US010932792B2

(12) United States Patent
Stokes et al.

(10) Patent No.: US 10,932,792 B2
(45) Date of Patent: Mar. 2, 2021

(54) SURGICAL CLIP APPLIER JAW ALIGNMENT

(71) Applicant: Ethicon LLC, Guaynabo, PR (US)

(72) Inventors: Michael J. Stokes, Cincinnati, OH (US); Chester O. Baxter, III, Loveland, OH (US); Carol J. Wynn, Kings Mills, OH (US)

(73) Assignee: Ethicon LLC, Guaynabo, PR (US)

( * ) Notice: Subject to any disclaimer, the term of this patent is extended or adjusted under 35 U.S.C. 154(b) by 349 days.

(21) Appl. No.: 15/674,086

(22) Filed: Aug. 10, 2017

(65) Prior Publication Data

US 2019/0046206 A1 Feb. 14, 2019

(51) Int. Cl.
| | | |
|---|---|---|
| *A61B 17/128* | (2006.01) | |
| *A61B 17/068* | (2006.01) | |
| *A61B 17/29* | (2006.01) | |
| *A61B 17/10* | (2006.01) | |
| *A61B 17/122* | (2006.01) | |

(52) U.S. Cl.
CPC ........ *A61B 17/1285* (2013.01); *A61B 17/068* (2013.01); *A61B 17/10* (2013.01); *A61B 17/1222* (2013.01); *A61B 2017/2933* (2013.01); *A61B 2017/2937* (2013.01)

(58) Field of Classification Search
CPC . A61B 17/1285; A61B 17/10; A61B 17/1222; A61B 2017/2937; A61B 2017/2933
See application file for complete search history.

(56) References Cited

U.S. PATENT DOCUMENTS

| | | | |
|---|---|---|---|
| 4,624,254 A | | 11/1986 | McGarry et al. |
| 5,171,249 A | * | 12/1992 | Stefanchik ......... A61B 17/1285 606/142 |

(Continued)

FOREIGN PATENT DOCUMENTS

| | | |
|---|---|---|
| CA | 2520746 A1 | 4/1997 |
| CN | 204636464 U | 9/2015 |

(Continued)

OTHER PUBLICATIONS

Extended European Search Report issued in European Application No. 18188291.1, dated Nov. 26, 2018, 11 pages.

(Continued)

*Primary Examiner* — Elizabeth Houston
*Assistant Examiner* — Michael G Mendoza
(74) *Attorney, Agent, or Firm* — Mintz Levin Cohn Ferris Glovsky and Popeo, P.C.

(57) ABSTRACT

A surgical clip applier and methods for applying surgical clips to a vessel, duct, shunt, etc., during a surgical procedure are provided. In one exemplary embodiment, a surgical clip applier is provided having a housing with a shaft extending therefrom with opposed jaws formed on a distal end thereof. A formed tube can extend along the shaft and it can be configured to advance over the jaws to move the jaws from an open position to a closed position to crimp the clip positioned therebetween. The surgical clip applier can include a variety of features to facilitate use of the device, including engagement features formed between the former tube and the jaws to prevent scissoring and misalignment of the jaws to ensure proper closure of the jaws.

16 Claims, 7 Drawing Sheets

(56) References Cited

U.S. PATENT DOCUMENTS

| | | | |
|---|---|---|---|
| 6,059,799 A | 5/2000 | Aranyi et al. | |
| 2010/0274263 A1 | 10/2010 | Disch et al. | |
| 2014/0005694 A1* | 1/2014 | Shelton, IV | A61B 17/1285 606/143 |
| 2016/0213377 A1* | 7/2016 | Shankarsetty | A61B 17/1285 |

FOREIGN PATENT DOCUMENTS

| | | |
|---|---|---|
| EP | 0834286 A1 | 4/1998 |
| EP | 2609875 A1 | 7/2013 |
| WO | 2003086207 A1 | 10/2003 |

OTHER PUBLICATIONS

International Preliminary Report on Patentability received for PCT International Application No. PCT/IB2018/055952, dated Feb. 20, 2020, 11 pages.

International Search Report and written opinion received for PCT Patent International Application No. PCT/IB2018/055952, dated Nov. 26, 2018, 13 pages.

* cited by examiner

SURGICAL CLIP APPLIER JAW ALIGNMENT

FIELD

Surgical devices and methods are provided for applying surgical clips to ducts, vessels, shunts, etc.

BACKGROUND

Surgical clip appliers are commonly used for ligating a blood vessel, a duct, shunt, or a portion of body tissue during surgery. Most clip appliers typically have a handle with an elongate shaft having a pair of movable opposed jaws formed on an end thereof for holding and forming a ligation clip therebetween. The jaws are positioned around the vessel or duct, and the clip is crushed or formed on the vessel by closing the jaws.

One problem with current clip appliers is that the jaws can become misaligned, and as a result may not sufficiently closing during use, creating surgical errors and/or prolong surgical procedures. Accordingly, there remains a need for improved methods and devices for applying surgical clips to vessels, ducts, shunts, etc.

SUMMARY

Various surgical instruments and methods are disclosed for applying a surgical clip to tissue, such as a vessel, duct, shunt, etc. In one embodiment, a surgical clip applier can include a housing, a shaft extending from the housing, and first and second jaws coupled to a distal end of the shaft. The first and second jaws can include opposed inward facing surfaces that define a clip track for receiving a distal-most clip from a plurality of clips disposed within the shaft. Furthermore, the first and second jaws can include outer chamfer contact surfaces. The surgical clip applier can further include a former member disposed around and proximal of the first and second jaws and movable distally such that inner contact surfaces of the former member can slidably engage the outer contact surfaces to cause the first and second jaws to move from an open configuration to a closed configuration for deforming a clip seated in the clip track. The inner contact surfaces on the former member and the outer contact surfaces on the first and second jaws can each be complementary and include at least a portion that is non-parallel with inner surfaces of the first and second jaws such that the former member vertically aligns the first and second jaws.

In one embodiment, the at least a portion that is non-parallel on the outer contact surfaces of the first and second jaws can include chamfer surfaces. Furthermore, the at least a portion that is non-parallel can include a curved portion. An entire outer contact surface of each the first and second jaws can extend at an angle less than 90 degrees relative to the inner surfaces of the first and second jaws. The at least a portion that is non-parallel on the outer contact surfaces of the first and second jaws can include a first chamfer formed on the outer contact surface of each of the first and second jaws, and a second chamfer can be formed on the outer contact surface of each of the first and second jaws.

The outer contact surfaces on the first and second jaws can have lower edges extending there along that are position a first distance apart, and upper edges extending there along that are position a second distance apart with the first distance being greater than the second distance. The inner contact surfaces on the former member can be configured to move the first and second jaws downward within the formed member as the former member is moved distally. The first and second jaws can be vertically aligned along a longitudinal plane of the former tube at least when the first and second jaws are in the closed configuration.

Another embodiment of a surgical clip applier can include a housing, a shaft extending from the housing, and first and second jaws coupled to a distal end of the shaft. The first and second jaws can include angled portions that diverge distally relative to one another. The first and second jaws can also have distal portions with opposed inward facing surfaces defining a clip track for receiving a distal-most clip from a plurality of clips disposed within the shaft. The angled portion can have a non-parallelogram cross-sectional shape. The surgical clip applier can further include a former member disposed proximal of the first and second jaws and movable distally around the angled portion of the first and second jaws to engage the angled portion to cause the first and second jaws to move from an open configuration to a closed configuration for deforming a clip seated in the clip track. The former tube can have inner engagement surfaces that complement the angled portions of the first and second jaws such that the former tube engages and vertically aligns the first and second jaws.

In one embodiment, the angled portions of the first and second jaws can each include an outer rounded side surface. Furthermore, the first and second jaws can be vertically aligned along a longitudinal plane of the former tube. The angled portions of the first and second jaws can include outer surfaces extending non-parallel to one another. The angled portions of the first and second jaws can include at least one chamfer surface extending there along. The inner engagement surfaces on the former tube can be configured to cause downward movement of the first and second jaws within the former tube as the formed tube is moved distally. The angled portions of the first and second jaws can include outer contact surfaces having lower edges extending there along that are positioned a first distance apart, and upper edges extending there along that are positioned a second distance apart with the first distance being greater than the second distance.

The present disclosure further provides devices and methods as claimed.

BRIEF DESCRIPTION OF THE DRAWINGS

The invention will be more fully understood from the following detailed description taken in conjunction with the accompanying drawings, in which.

DETAILED DESCRIPTION

Figure 1:
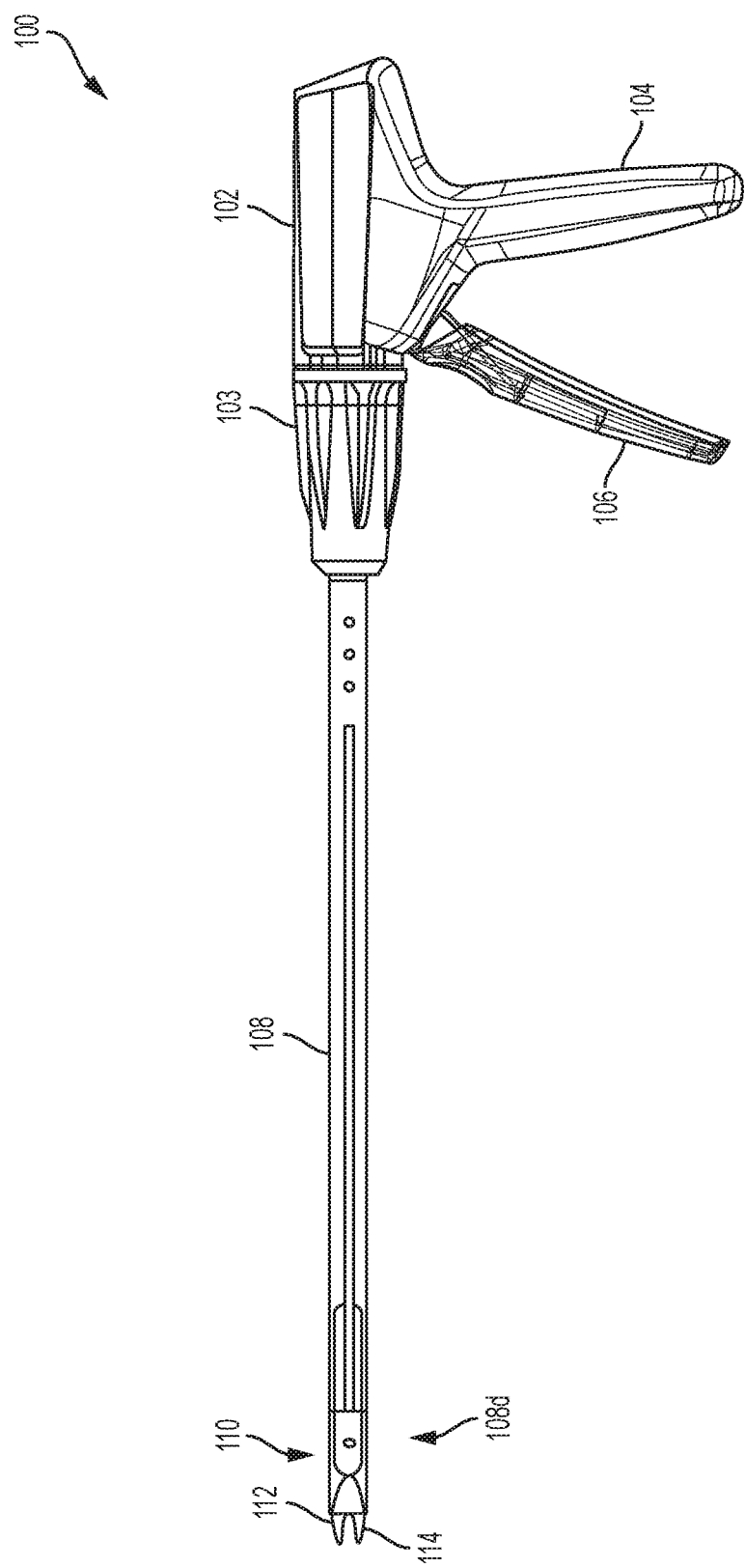
FIG. 1 is a side view of one exemplary embodiment of a surgical clip applier.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Surgical clip appliers and methods are provided for applying surgical clips to tissue, such as a vessel, duct, shunt, etc., during a surgical procedure. The surgical clip applier can include a pair of jaws positioned at a distal end of a shaft extending from a housing, and the pair of jaws can be configured to pivot from an open configuration to a closed configuration to form surgical clips positioned between the jaws. In order for the surgical clips to be properly formed around the tissue, the jaws should at least be properly aligned. However, various forces can be applied to the jaws during use that can force the jaws out of alignment. If the jaws become misaligned, the jaws can scissor during closing, e.g., where one jaws moves past or over the other jaw, resulting in a malformed clip.

Accordingly, various embodiments of surgical clip appliers are provided having features that can assist with aligning the jaws, such as maintaining alignment of the jaws along a single plane thereby assisting with preventing the jaws from scissoring when in the closed configuration. A person skilled in the art will appreciate that the surgical clip applier can include all or only some of the features described herein in any combination and/or can include a variety of other features known in the art. The surgical clip appliers described herein are merely intended to represent certain exemplary embodiments.

FIGS. 1-4B illustrate one embodiment of a surgical clip applier 100. As shown, the surgical clip applier 100 generally includes a housing 102 having a stationary handle 104 and a movable handle or trigger 106 that is pivotally coupled to the housing 102. An elongate shaft 108 extends distally from the housing 102 and includes a jaw assembly 110 formed on a distal end 108d thereof and including first and second jaws 112, 114 that are movable between open and closed positions. The first and second jaws 112, 114 include opposed inward facing surfaces and each inward facing surface has a clip track formed there along for receiving and guiding legs of a clip into the first and second jaws 112, 114. The elongate shaft 108 can be rotated with respect to the housing 102 via a rotation knob 103.

Figure 2:
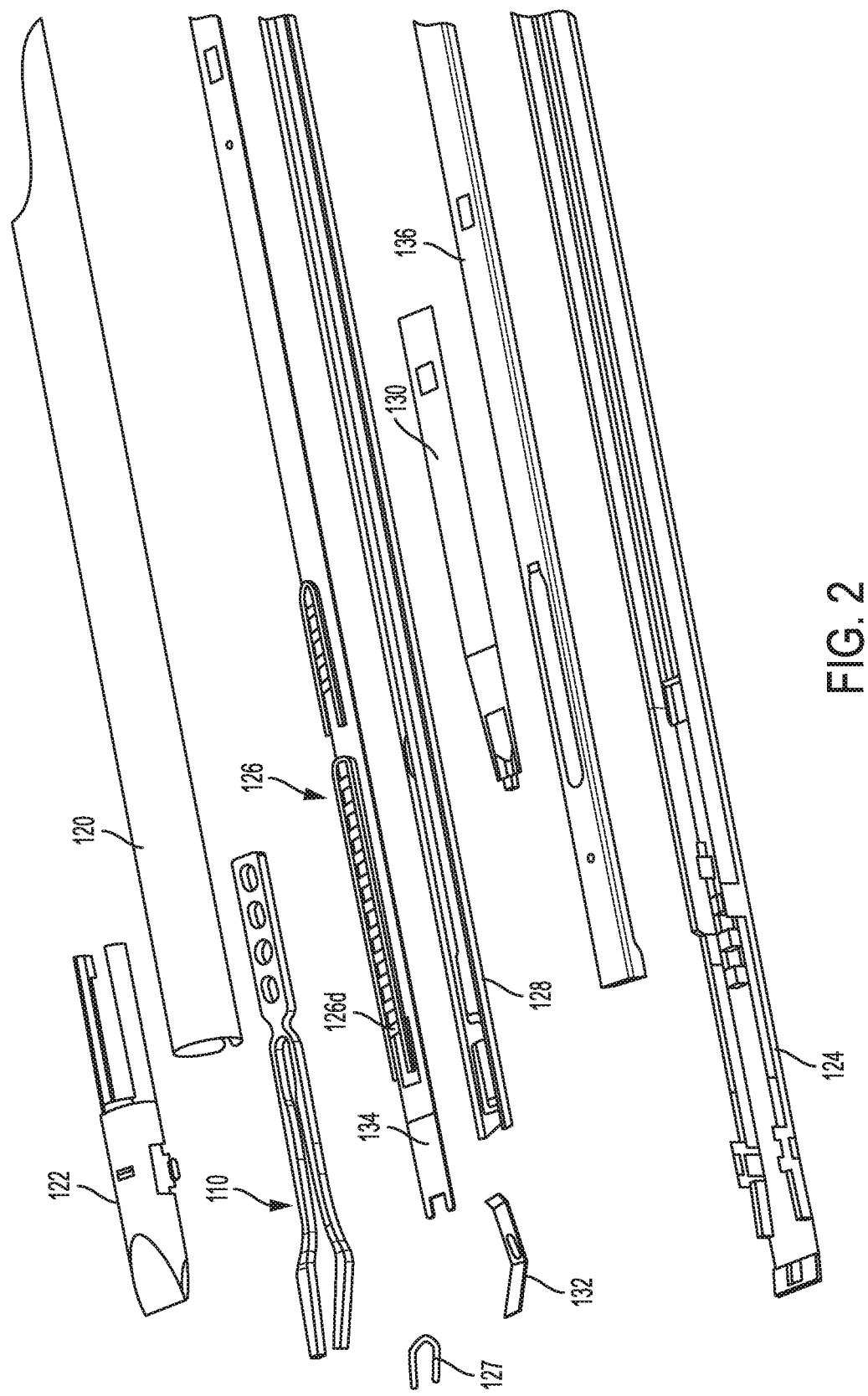
FIG. 2 is an exploded view of a distal portion of the surgical clip applier of FIG. 1.
Figure 3:
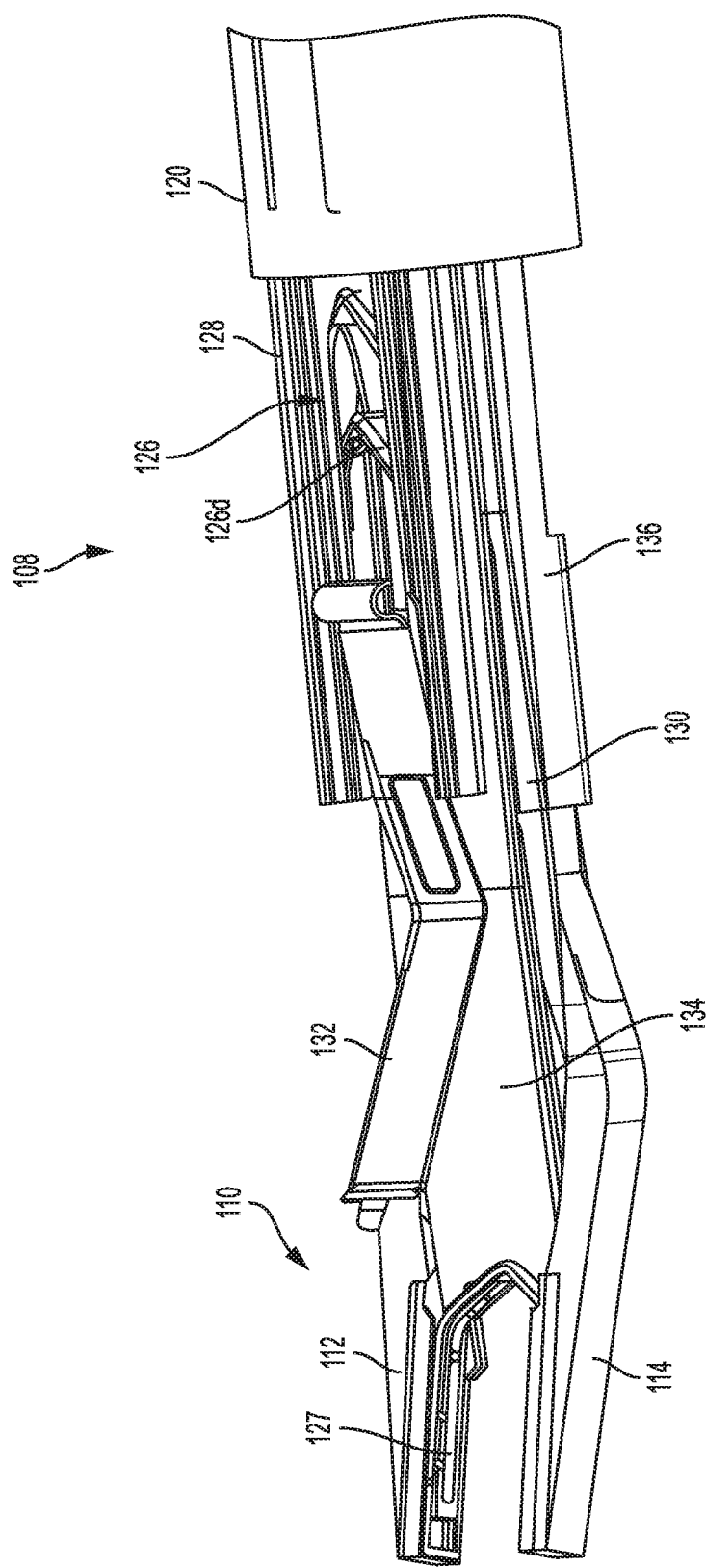
FIG. 3 is a perspective view of a distal portion of the surgical clip applier of FIG. 1.

As shown in FIGS. 2 and 3, the elongate shaft 108 can include an outer support tube 120, an upper shroud 122 coupled distally to the outer support tube 120, and a lower shroud 124. The outer support tube 120 and the upper and lower shrouds 122, 124 form an outer casing of the shaft 108. As shown in FIGS. 2 and 3, a clip stack 126 including multiple surgical clips is disposed within a clip track or holder 128 of the shaft 108 proximal to the first and second jaws 112, 114, and is biased distally. A floor 130 extends beneath the clip stack 126 for maintaining the clip stack 126 in alignment within the shaft 108, and for guiding a distal-most clip 126d into the jaws 112, 114. A lifter spring 132 is positioned just proximal to the jaws 112, 114 and distal to the clip stack 126 for preventing distal movement of the clip stack 126, with the distal-most clip 126d disposed around the lifter spring 132. A feeder bar 134 extends through the elongate shaft 108 for feeding the distal-most clip 126d into the jaws. As shown in FIG. 3 illustrating the clip applier 100 with the upper and lower shrouds 122, 124 removed, a former tube 136 extends around a proximal end of the jaws 112, 114 and is movable distally to cam the jaws 112, 114 to a closed position for forming a clip 127 disposed therebetween.

Figure 4A:
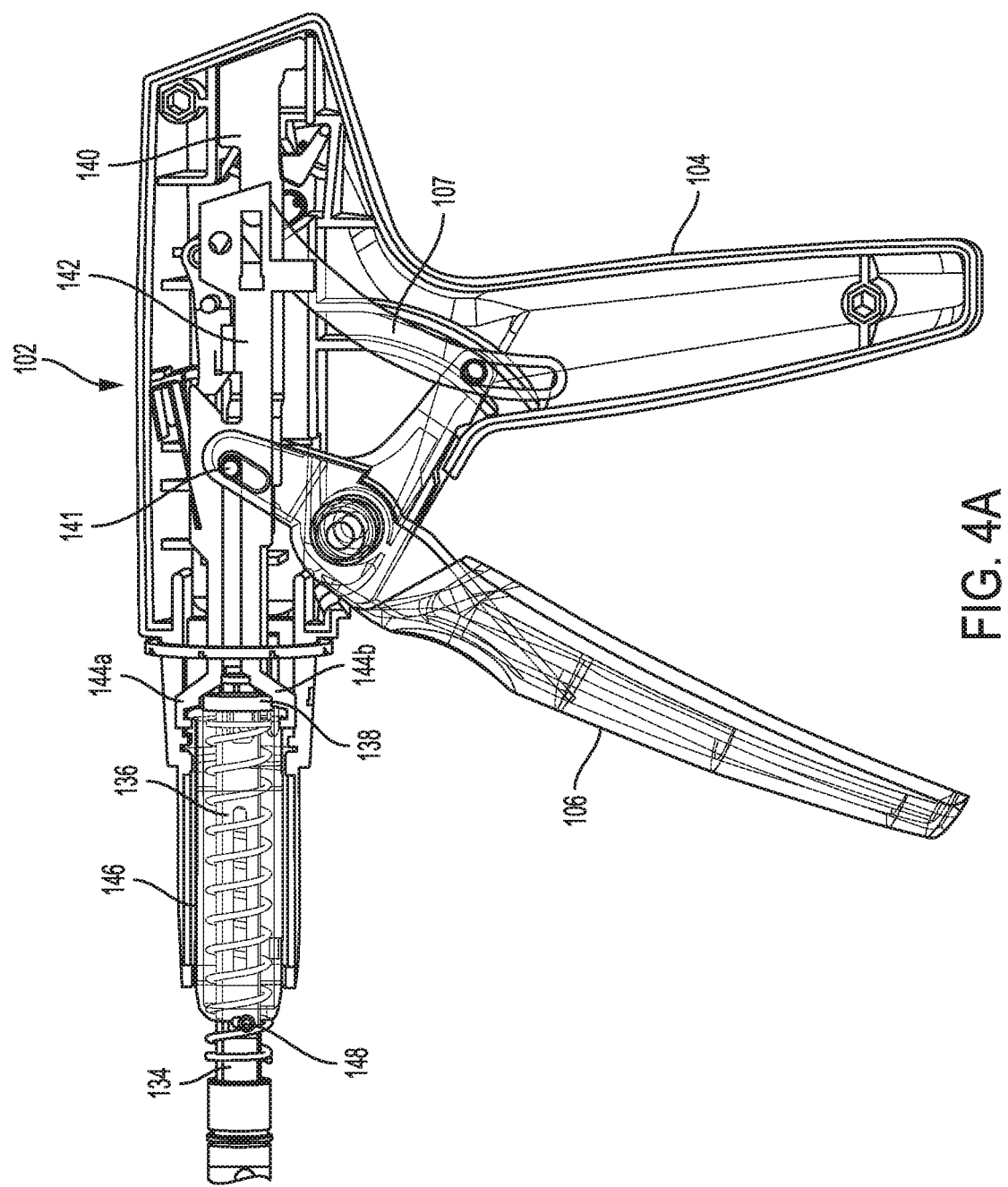
FIG. 4A is a perspective, partially transparent view of a proximal portion of the surgical clip applier of FIG. 1.
Figure 4B:
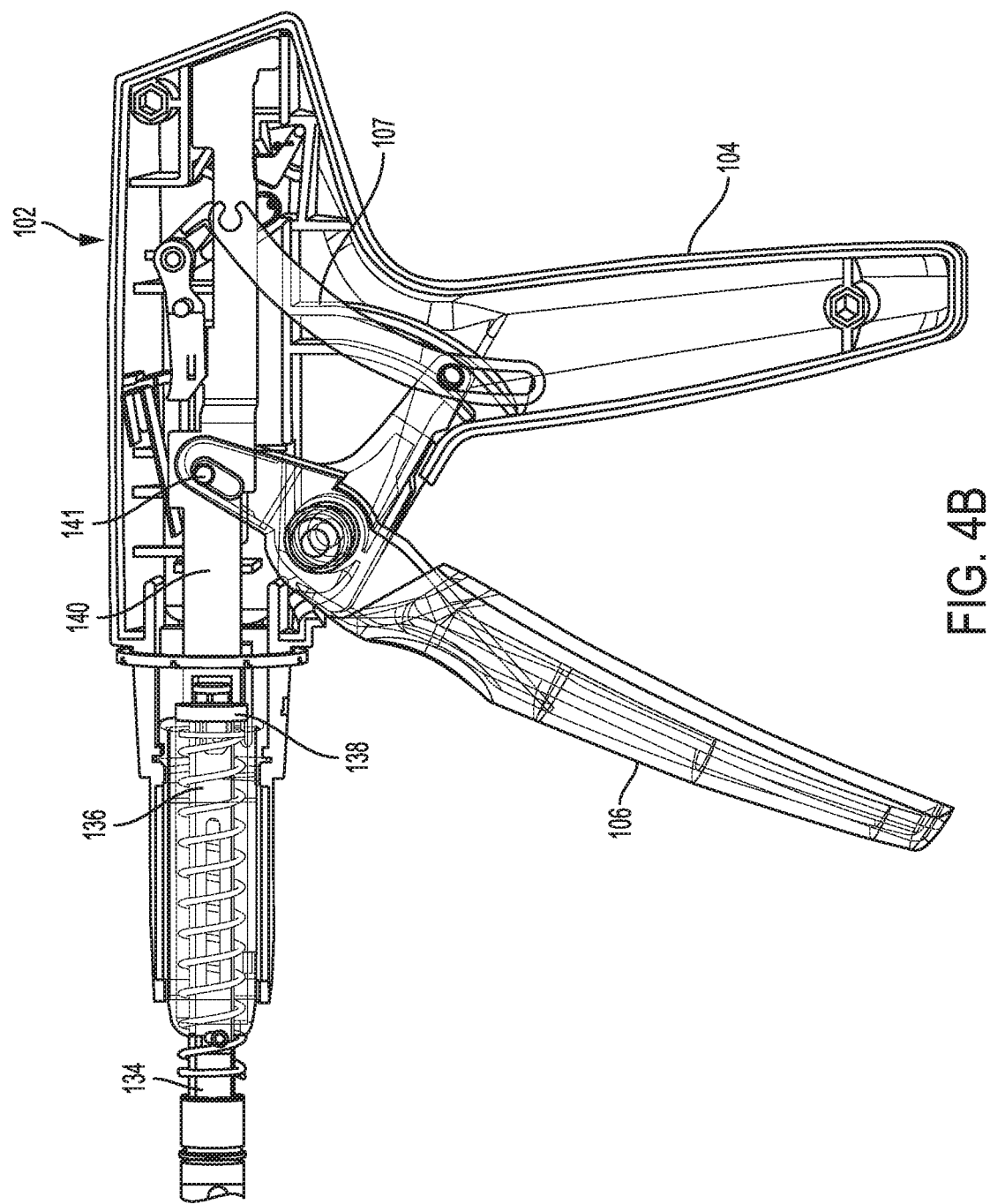
FIG. 4B is another perspective view of the proximal portion of the surgical clip applier of FIG. 1.

The surgical clip applier 100 has a clip forming assembly including various components that operate together to close the jaws 112, 114 when the trigger 106 is activated to thereby cause a clip (e.g., clip 127) disposed in the jaws to be applied (formed) to the tissue. The clip forming assembly encompasses the former tube 136 and other components that are coupled to the trigger 106 configured to be activated to move the former tube 136 distally to thereby close the jaws 112, 114. A clip advancing assembly of the surgical clip applier 100 includes the feeder bar 134 that is also coupled to the trigger 106, via a link 107 extending proximally from the trigger 106, as shown in FIGS. 4A and 4B. In this way, when the trigger 106 is activated, the feeder bar 134 is caused to move proximally, opposite to a distal direction in which the former tube 136 is moved upon activation of the trigger 106.

The clip forming and clip advancing assemblies can have any suitable configurations. For example, in the illustrated embodiment, as shown in FIGS. 4A and 4B, the former tube 136 of the clip forming assembly is coupled, via an inner coupling 138, to a former plate 140 in the housing 102 that is, in turn, coupled to the trigger 106 via a pin 141, and the feeder bar 134 of the clip advancing assembly is coupled to the trigger 106 via a feeder plate 142 that is also coupled to the trigger 106, via the link 107. As shown in FIG. 4A, the feeder plate 142 has arms 144a, 144b at a distal end thereof that are disposed over and mate with a proximal end of an outer coupling 146 (shown partially transparent). A connecting pin 148 at a distal end of the outer coupling 146 attaches the feeder bar 134 to the outer coupling 146. FIGS. 4A and 4B illustrate the handle 102 with part of an outer casing removed, and FIG. 4B shows the handle housing 102 without the feeder plate 142, for illustration purposes only. It should be appreciated that the surgical clip applier 100 can include various other components and assemblies that are not described herein for the sake of simplicity.

In use, when the trigger 106 of the housing 102 is activated (e.g., moved towards the stationary handle 104), the former plate 140 of the clip forming assembly is advanced distally to cause the former tube 136 to advance distally over the jaws 112, 114, thereby camming the jaws 112, 114 to the closed position. At the same time, the feeder plate 142 of the clip advancing assembly is moved proximally, thereby pulling the feeder bar 134 proximally to position the feeder bar 134 proximal of the distal-most clip 126d of the clip stack 126. Once the clip 127, disposed in the jaws 112, 114 such that clip's legs are received within the clip track of each of the jaws, is fully formed, the trigger 106 is released, which causes the clip forming assembly to move proximally while the clip advancing assembly moves distally. FIG. 2 shows the clip 127 in an original, pre-formed configuration. The proximal movement of the clip forming assembly causes the former tube 136 to retract relative to the jaws, thus allowing the jaws 112, 114 to move to the original open position, thereby releasing the formed clip. The distal movement of the clip advancing assembly causes the feeder bar 134 to move distally, and the feeder bar 134 thereby pushes the distal-most clip 126d distally, overcoming the biasing force of the lifter spring 132 and causing the lifter spring 132 to deflect out of the way, thereby allowing the distal-most clip 126d to be advanced into the jaws 112, 114. In this way, the distal-most clip becomes positioned in the jaws' clip track, like the clip 127 in FIG. 3. The floor 130 helps guide the distal-most clip into the clip tracks of the jaws 112, 114.

A person skilled in the art will appreciate that, while a trigger is shown and described, the clip appliers disclosed herein need not include a trigger, and can have a variety of other actuation mechanisms. For example, the clip applier can be powered and can include an actuation button for actuating a motor to control firing of the device. In other embodiments, the housing can be configured to couple to a robotic system, such that actuation of the device is controlled through the robotic system.

As indicated above, scissoring or misalignment of the jaws during closing can prevent proper formation of a clip positioned between the jaws and/or can prevent the jaws from sufficiently grasping tissue. Various embodiments of the former tube and jaws of the clip applier are thus provided to help prevent misalignment of the jaws during closing.

Figure 5B:
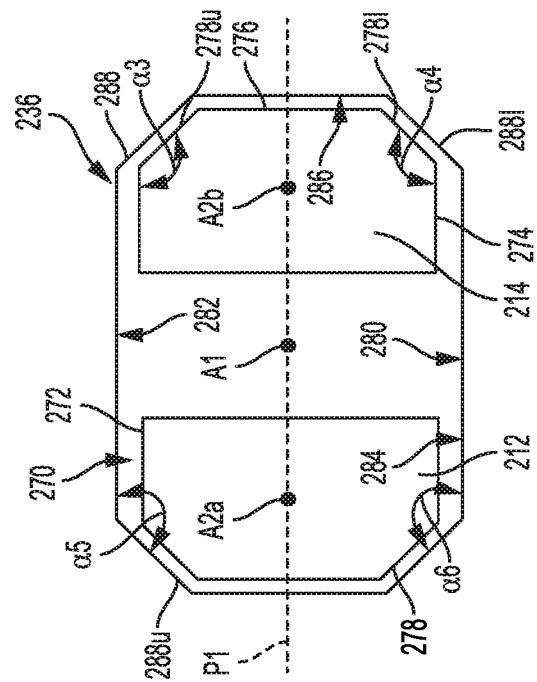
FIG. 5B is a cross-sectional view of the former tube and jaws of FIG. 5A showing chamfer surfaces of the jaws and tapered surfaces of the former tube.
Figure 5A:
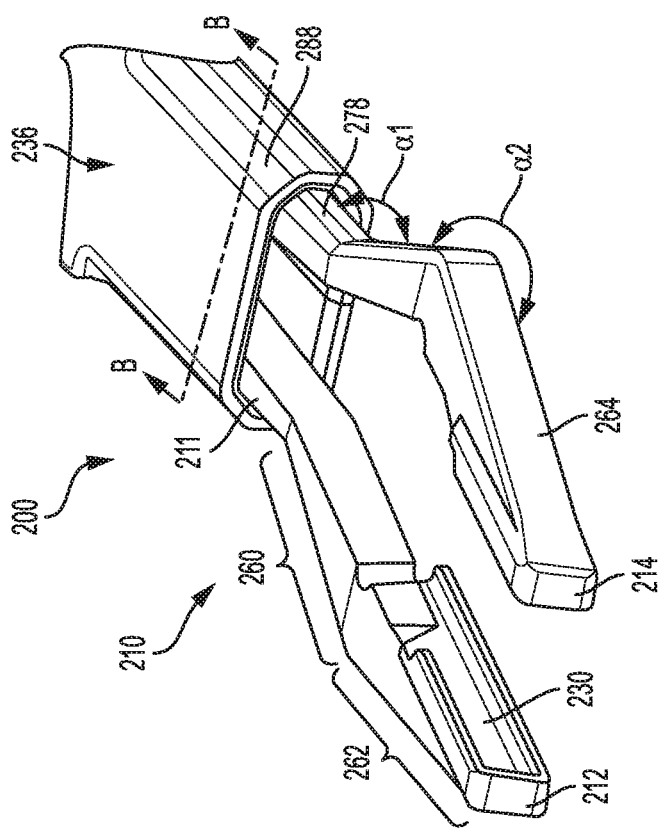
FIG. 5A is a partial top perspective view of an embodiment of a former tube positioned around a pair of jaws of a clip applier.

FIGS. 5A-5B illustrate one embodiment of a jaw assembly 210 and a former tube 236 of a clip applier 200 that includes engagement surfaces between the jaw assembly 210 and the former tube 236 that assist with vertically aligning a pair of jaws 212, 214 of the jaw assembly 210, including preventing misalignment of the jaws 212, 214 during closing.

As shown in FIG. 5A, the former tube 236 can be positioned around a proximal part 211 of the jaw assembly 210 (only a portion of the proximal part 211 is shown). The proximal part 211 can distally split into two arms that form the jaws 212, 214. The former tube 236 can be advanced distally (e.g., upon activation of the trigger 106, as shown in FIG. 4A) to cam the jaws 212, 214 to a closed position for forming a clip therebetween.

As shown in FIG. 5A, the jaws 212, 214 can include an angled portion or region 260 that extends distally from the proximal part 211 at an angle α1 (e.g., the angle being within a range of approximately 150 degrees to approximately 170 degrees) and in a direction away from a longitudinal axis A1 of the former tube 236, as shown in FIG. 5B. As such, the angled regions 260 diverge distally away from one another. The jaws 212, 214 can also include a distal portion 262 having an outer distal surface 264 that extends distally from the angled region 260 at an angle α2 (e.g., the angle being within a range of approximately 205 degrees to approximately 215 degrees) and in a direction towards the longitudinal axis A1 of the former tube 236. Additionally, the distal portions 262 of the jaws 212, 214 can include opposed inward facing surfaces 230 that can extend parallel to the longitudinal axis A1 of the former tube 236. Each inward facing surface 230 can have a clip track formed there along for receiving and guiding legs of a clip into the first and second jaws 112, 114. As shown in FIG. 5A, when the jaws 212, 214 are open, the proximal part 211 of the jaw assembly 210 can extend approximately parallel to the longitudinal axis A1 of the former tube 236.

As shown in FIG. 5B, the jaws 212, 214 can include outer contact surfaces 270 that are configured to engage inner contact surfaces 280 of the former tube 236, and such engagement can assist with aligning longitudinal axis A2a, A2b of the jaws 212, 214, respectively, along a longitudinal plane P1 of the former tube 236. Such alignment of the longitudinal axis A2a, A2b of the jaws 212, 214 with the longitudinal plane P1 of the former tube 236 can assist with preventing misalignment of the jaws 212, 214 when in the closed position. In the illustrated embodiment, the outer contact surfaces 270 of the jaws 212, 214 can include top surfaces 272, bottom surfaces 274, and outer side surfaces 276, as well as chamfer surfaces 278 that extend between the top surfaces 272 and outer side surfaces 276 and between the bottom surfaces 274 and outer side surfaces 276. The inner contact surfaces 280 of the former tube 236 can have a complementary shape with an inner top surface 282, an inner bottom surface 284, and opposed inner side surfaces 286. Additionally, the inner contact surfaces 280 can include tapered surfaces 288 that extend between the inner top surface 282 and the opposed inner side surfaces 286, as well as between the inner bottom surface 284 and the opposed inner side surfaces 286. The resulting cross-sectional shape of the angled region 260 of each jaw 212, 214 thus has a shape other than a parallelogram.

The chamfer surfaces 278 can include upper chamfer surfaces 278u that extend from the top surfaces 272 at a angle α3 (e.g., the angle being within a range of approximately 100 degrees to approximately 170 degrees) and lower chamfer surfaces 278l that extend from the bottom surfaces 274 at an angle α4 (e.g., the angle being within a range of approximately 100 degrees to approximately 170 degrees). The tapered surfaces 280 can include upper tapered surfaces 288u that extend from the inner top surface 282 at an angle α5 (e.g., the angle being within a range of approximately 100 degrees to approximately 170 degrees) and lower taper surfaces 288l that extend from the inner bottom surface 284 at an angle α6 (e.g., the angle being within a range of approximately 100 degrees to approximately 170 degrees). The chamfer surfaces 278 and tapered surfaces 288 can extend at a same or similar angle thereby positioning the chamfer surfaces 278 and tapered surfaces 288 parallel to each other for allowing the chamfer surfaces 278 and tapered surfaces 288 to longitudinally slidably engage one another. For example, the upper chamfer surfaces 278u can be positioned parallel to the upper tapered surfaces 288u, and the lower chamfer surfaces 278l can be positioned parallel to the lower tapered surfaces 288l, as shown in FIG. 5B. Furthermore, the upper chamfer and tapered surfaces 278u, 288u can extend at a same or different angle compared to the lower chamfer and tapered surfaces 278l, 288l.

With the chamfer surfaces 278 and tapered surfaces 288 able to longitudinally slidably engage as the former tube 236 distally advances to force the jaws 212, 214 closed, the upper tapered surfaces 288u can guide the jaws 212, 214 downward towards the longitudinal plane P1 of the former tube 236, and the lower tapered surfaces 288l can guide the jaws 212, 214 upward toward the longitudinal plane P1. As such, the upper and lower tapered surfaces, 288u, 288l can act in opposing directions against the chamfer surfaces 278 of the jaws 212, 214 to stabilize the position of the jaws 212, 214 such that the longitudinal axis A2a, A2b of the jaws 212, 214 can align with the longitudinal plane P1 of the former tube 236. The jaws 212, 214 can be aligned with each other as the former tube 236 distally advances, thereby closing the jaws 212, 214 in alignment.

As shown in FIG. 5A, the chamfer surfaces 278 can extend along the angled region 260 to allow the tapered surfaces 288 of the former tube 236 to extend around and engage the chamfer surfaces 278 of the jaws 212, 214 along the length of the angled region 260. As such, the tapered surfaces 288 of the former tube 236 can engage the chamfer surfaces 278 of the jaws 212, 214 throughout the closing of the jaws 212, 214. In some embodiments, the chamfer surfaces 278 can extend along at least a part of the proximal part 211 of the jaws 212, 214, which can allow the former tube 236 to assist with maintaining alignment of the jaws 212, 214 even while the former tube 236 is in an original non-activated position (e.g., prior to activation of the trigger 106).

During manufacturing, a dimensional tolerance can be included in the manufacturing of the jaws 212, 214 and the former tube 236 to ensure the jaws 212, 214 can be assembled at least partially within and slidably engaged with the former tube 236. As such, when assembled, a first gap can exist between the top surfaces 272 of the jaws 212, 214 and the inner top surface 282 of the former tube 236 and/or a second gap can exist between the bottom surfaces 274 of the jaws 212, 214 and the inner bottom surface 284 of the former tube 236. Without the engagement between the chamfer and tapered surfaces 278, 288 that guide the longitudinal axis A2a, A2b of the jaws 212, 214 to align with the longitudinal plane P1, the jaws 212, 214 can become misaligned, such as one jaw pivoting upward to close the first gap and the other jaw pivoting downward to close the second gap. Such movement by the jaws can result in misalignment and scissoring of the jaws 212, 214, which can prevent formation of a clip positioned therebetween. The configurations of the former tube 236 and jaws 212, 214 illustrated and described above with regard to FIGS. 5A-5B, as well as the resulting engagement between the former tube 236 and jaws 212, 214, can thus assist with aligning the jaws 212, 214 even with such first and second gaps. This can occur at least because alignment of the jaws is not dependent upon engagement between the inner top and bottom surfaces 282, 284, and is, instead, dependent at least in part by the engagement between the chamfer and tapered surfaces 278, 288, as described above. Various other embodiments of the jaws and former tube that can assist with aligning the jaws have been contemplated, some of which are described in detail below.

Figure 6:
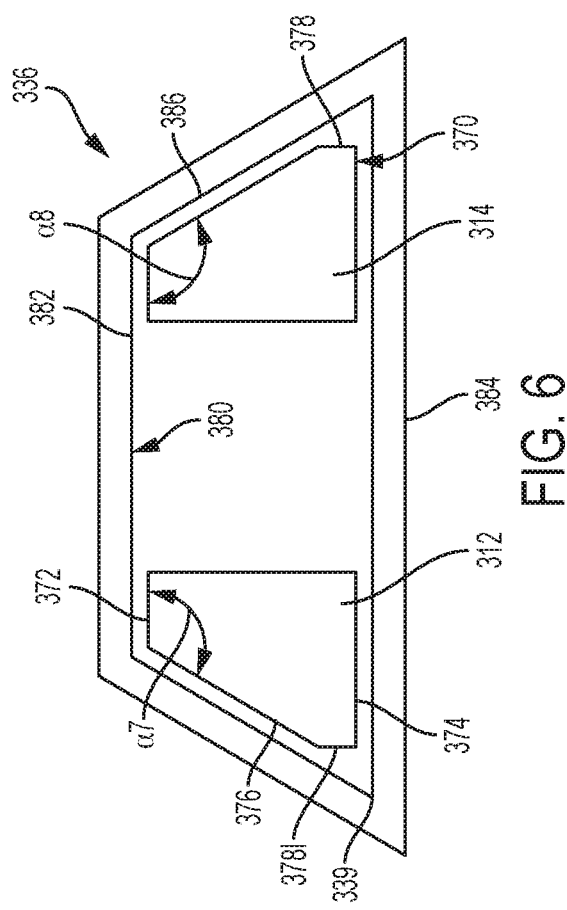
FIG. 6 is a cross-sectional view of another embodiment of a former tube positioned around a pair of jaws of a clip applier showing angled outer side surfaces of the jaws and angled inner side surfaces of the former tube.

FIG. 6 illustrates a cross-sectional view of another embodiment of a clip applier showing an engagement between a former tube 336 and jaws 312, 314 that can assist with aligning the jaws 312, 314 at least when closed. As shown in FIG. 6, the jaws 312, 314 can include outer contact surfaces 370 that are configured to engage inner contact surfaces 380 of the former tube 336. The outer contact surfaces 370 of the jaws 312, 314 can include top surfaces 372, bottom surfaces 374, and outer angled side surfaces 376, resulting in a non-parallelogram cross-sectional shape. For example, as a result of the outer angled side surfaces 376, the bottom surfaces 374 can each include lower edges extending there along that are positioned a first distance apart. Additionally, the top surfaces 372 can each include upper edges extending there along that are positioned a second distance apart, and the second distance can be less than the first distance. In some embodiments, the outer contact surfaces 370 can include at least one chamfer surface 378, such as lower chamfer surfaces 3781 shown in FIG. 6 that extends between the bottom and outer angled side surfaces 374, 376. For example, the outer angled side surfaces 376 can extend from the top surfaces 372 at an angle α7 (e.g., the angle being within a range of approximately 100 degrees to approximately 170 degrees).

As shown in FIG. 6, the inner contact surfaces 380 of the former tube 336 can include an inner top surface 382, an inner bottom surface 384, and inner angled side surfaces 386. For example, the inner angled side surfaces 386 can extend from the inner top surface 382 at an angle α8 (e.g., the angle being within a range of approximately 100 degrees to approximately 170 degrees). Although the outer and inner angled side surfaces 376, 386 can extend at a variety of angles, such as described herein, the outer and inner angled side surfaces 376, 386 can extend at the same or similar angle thereby positioning the outer and inner angled side surfaces 376, 386 parallel to each other for allowing the outer and inner angled side surfaces 376, 386 to slidably engage one another.

With the outer and inner angled side surfaces 376, 386 able to longitudinally slidably engage as the former tube 336 distally advances to force the jaws 312, 314 closed, the inner angled side surfaces 386 can guide the jaws 312, 314 downward towards the inner bottom surface 384 of the former tube 336. As such, both jaws 312, 314 can be controlled vertically by the inner angled side surfaces 386 and guided downward along the inner angled side surfaces 386 until the bottom surfaces 374 of the jaws 312, 314 mate against the inner bottom surface 384 of the former tube 336. As shown in FIG. 6, the inner bottom surface 384 can be flat and horizontal thereby allowing the jaws 312, 314 to be aligned when the bottom surfaces 374 are mated against the inner bottom surface 384. The jaws 312, 314 can thus be aligned with each other as the former tube 336 distally advances, including when the jaws 312, 314 are closed. The chamfer surfaces of the 378 jaws can, for example, prevent an edge (e.g., an acute-angled edge formed between adjacent surfaces) of either jaw 312, 314 from becoming wedged or stuck into a corner (e.g., inner lower acute-angled corner 339) of the former tube 336. Such wedging can be a result of increased frictional forces that can interfere with or prevent movement of the former tube 336 relative to the jaws 312, 314. For example, if angle α7 (e.g., defining upper edges) of the jaws 312, 314 is larger than angle α8 (e.g., defining upper corners) of the former tube 336 the upper edges of the jaws 312, 314 can become wedged or stuck to the upper corners of the former tube 336, thereby preventing movement of the jaws 312, 314.

Figure 7:
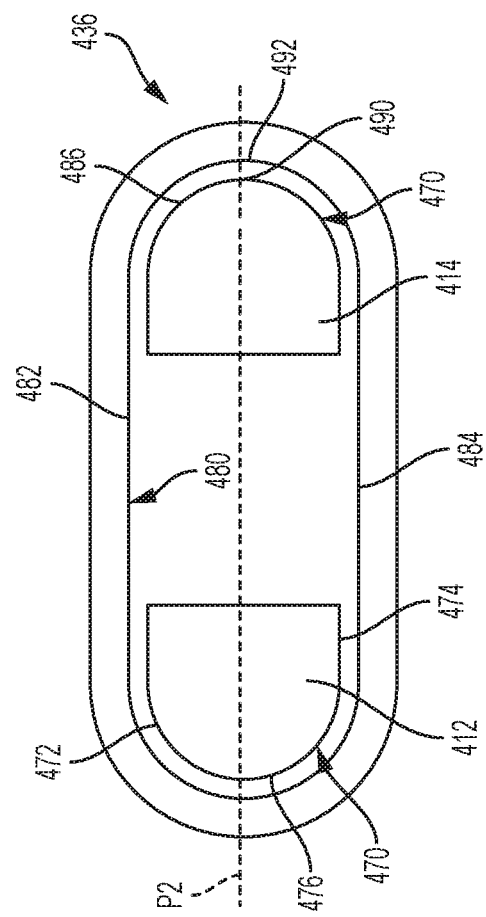
FIG. 7 is a cross-sectional view of another embodiment of a former tube positioned around a pair of jaws of a clip applier showing rounded outer side surfaces of the jaws and rounded inner side surfaces of the former tube.

FIG. 7 illustrates a cross-sectional view of another embodiment of a clip applier showing an engagement between a former tube 436 and jaws 412, 414 that can assist with aligning the jaws 412, 414 at least when closed. As shown in FIG. 7, the jaws 412, 414 can include outer contact surfaces 470 that are configured to engage inner contact surfaces 480 of the former tube 436. The outer contact surfaces 470 of the jaws 412, 414 can include top surfaces 472, bottom surfaces 474, and outer rounded side surfaces 476.

As shown in FIG. 7, the inner contact surfaces 480 of the former tube 436 can include an inner top surface 482, an inner bottom surface 484, and inner rounded side surfaces 486. For example, the outer and inner rounded side surfaces 476, 486 can have a radius. The outer and inner rounded side surfaces 476, 486 can have the same or similar radii thereby guiding a most convex part 490 of each of the outer rounded side surfaces 476 towards a most concave part 492 of each of the inner rounded side surfaces 486. The most concave parts 492 of the inner rounded side surfaces 486 can be aligned thereby aligning the jaws 412, 414 when the most convex parts 490 of the outer rounded surfaces 476 are aligned with the most concave parts 492 of the inner rounded side surfaces 486. For example, as shown in FIG. 7, the most concave parts 492 of the inner rounded side surfaces 486 can be positioned along a longitudinal plane P2 of the former tube 436. As such, the jaws 412, 414 can be aligned along the longitudinal plane P2 at least when the jaws 412, 414 are closed.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Reconditioning a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical clip applier, comprising:
   a housing;
   a shaft extending from the housing;
   first and second jaws coupled to a distal end of the shaft, the first and second jaws having opposed inward facing surfaces defining a clip track for receiving a distal-most clip from a plurality of clips disposed within the shaft, the first and second jaws having outward facing contact surfaces, at least a portion of the outward facing contact surfaces of the first and second jaws comprising chamfer surfaces; and
   a former member disposed around and proximal of the first and second jaws and movable distally such that inward facing contact surfaces of the former member slidably engage the outward facing contact surfaces to cause the first and second jaws to move from an open configuration to a closed configuration for deforming a clip seated in the clip track, at least a portion of the inward facing contact surfaces of the former member comprising tapered surfaces that complement the chamfer surfaces of the first and second jaws, the former member having an octagonal cross-section at a location perpendicular to a longitudinal axis of the former member where the former member slidably engages the first and second jaws.

2. The surgical clip applier of claim 1, wherein at least a portion on the outward facing contact surfaces comprises a curved portion.

3. The surgical clip applier of claim 1, wherein an entire outward facing contact surface of each the first and second jaws extends at an angle less than 90 degrees relative to the inner surfaces of the first and second jaws.

4. The surgical clip applier of claim 1, wherein the chamfer surface of each of the first and second jaws comprises a first chamfer formed on the outward facing contact surface of each of the first and second jaws, and a second chamfer formed on the outward facing contact surface of each of the first and second jaws.

5. The surgical clip applier of claim 1, wherein the outward facing contact surfaces on the first and second jaws have lower edges extending therealong that are position a first distance apart, and upper edges extending therealong that are position a second distance apart, the first distance being greater than the second distance.

6. The surgical clip applier of claim 5, wherein the inward facing contact surfaces on the former member are configured to move the first and second jaws downward within the former member as the former member is moved distally.

7. The surgical clip applier of claim 1, wherein the first and second jaws are vertically aligned along a longitudinal plane of the former tube at least when the first and second jaws are in the closed configuration.

8. The surgical clip applier of claim 1, wherein each of the outward facing contact surfaces on the first and second jaws comprises a top surface, an upper chamfer surface, an outer side surface, a lower chamfer surface, and a bottom surface; and
   wherein the inward facing contact surfaces on the former member comprise an inner top surface, upper tapered surfaces, inner side surfaces, lower taper surfaces, and an inner bottom surface.

9. The surgical clip applier of claim 1, wherein each of the former member, the first jaw, and the second jaw has a non-parallelogram cross-sectional shape at the location perpendicular to the longitudinal axis of the former member where the former member slidably engages the first and second jaws.

10. A surgical clip applier, comprising:
    a housing;
    a shaft extending from the housing;
    first and second jaws coupled to a distal end of the shaft, the first and second jaws having outward facing chamfered angled portions that diverge distally relative to one another, and the first and second jaws having distal portions with opposed inward facing surfaces defining a clip track for receiving a distal-most clip from a plurality of clips disposed within the shaft, the angled portion having a non-parallelogram cross-sectional shape, the first and second jaws have chamfered proximal portions that are proximal to the outward facing chamfered angled portions, each of the chamfered proximal portions comprising a top surface, a first chamfer surface, an outer side surface, a second chamfer surface, and a bottom surface; and a former tube disposed proximal of the first and second jaws and movable distally around the angled portion of the first and second jaws to engage the angled portion to cause the first and second jaws to move from an open configuration to a closed configuration for deforming a clip seated in the clip track, the former tube having tapered inward facing engagement surfaces that complement the outward facing chamfered angled portions of the first and second jaws such that the former tube engages and vertically aligns the first and second jaws, the tapered inward facing engagement surfaces extending parallel to each complementary surface of the chamfered proximal portions of the first and second jaws.

11. The surgical clip applier of claim 10, wherein the first and second jaws are vertically aligned along a longitudinal plane of the former tube.

12. The surgical clip applier of claim 10, wherein the angled portions of the first and second jaws include outward facing surfaces extending non-parallel to one another.

13. The surgical clip applier of claim 10, wherein the inward facing engagement surfaces on the former tube are configured to cause downward movement of the first and second jaws within the former tube as the formed tube is moved distally.

14. The surgical clip applier of claim 10, wherein the angled portions of the first and second jaws include outward facing contact surfaces having lower edges extending therealong that are positioned a first distance apart, and upper edges extending therealong that are positioned a second distance apart, the first distance being greater than the second distance.

15. The surgical clip applier of claim 10, wherein the former tube has an octagonal cross-section at the location perpendicular to the longitudinal axis of the former tube where the former tube surrounds the chamfered proximal portions of the first and second jaws.

16. The surgical clip applier of claim 10, wherein the tapered inward facing engagement surfaces of the former tube comprises an inner top surface, upper tapered surfaces, inner side surfaces, lower taper surfaces, and an inner bottom surface, and each of the tapered inward facing engagement surfaces extends parallel to each complementary surface of the chamfered proximal portions of the first and second jaws.

* * * * *